United States Patent

Maurer et al.

[11] 4,168,304
[45] Sep. 18, 1979

[54] COMBATING PESTS WITH 4-SUBSTITUTED-PYRIMIDIN-6-YL (THIONO)-PHOSPHORIC (PHOSPHONIC) ACID ESTERS OR ESTER AMIDES

[75] Inventors: Fritz Maurer; Hans-Jochem Riebel, both of Wuppertal; Rolf Schröder, Velbert; Ingeborg Hammann, Cologne; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 869,066

[22] Filed: Jan. 12, 1978

[30] Foreign Application Priority Data

Jan. 27, 1977 [DE] Fed. Rep. of Germany ....... 2703310

[51] Int. Cl.$^2$ .......................... A01N 9/36; C07F 9/65
[52] U.S. Cl. ...................................... 424/200; 544/243
[58] Field of Search .................... 260/251 P, 256.4 E, 260/256.5 R; 424/200; 544/243

[56] References Cited

U.S. PATENT DOCUMENTS

| | | | |
|---|---|---|---|
| 2,754,243 | 7/1956 | Gysin et al. | 424/200 |
| 3,205,231 | 9/1965 | Fest | 260/251 P |
| 3,216,894 | 11/1965 | Lorenz et al. | 424/200 |

Primary Examiner—Donald G. Daus
Assistant Examiner—D. Rivers
Attorney, Agent, or Firm—Sprung, Felfe, Horn, Lynch & Kramer

[57] ABSTRACT

4-Substituted-pyrimidin-6-yl (thiono)-phosphoric (phosphonic) acid esters or ester-amides of the formula

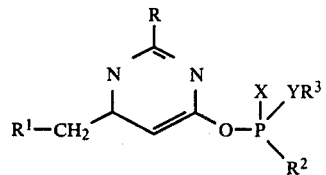

in which
  R represents hydrogen, alkyl, alkoxy, alkylthio or alkylamino,
  R$^1$ represents halogen, alkoxy, alkylthio or alkylamino,
  R$^2$ represents alkyl, alkoxy, alkylamino or phenyl,
  R$^3$ represents alkyl and
  X and Y, which may be identical or different, represent oxygen or sulphur, which possess arthropodicidal and nematicidal properties.

10 Claims, No Drawings

COMBATING PESTS WITH 4-SUBSTITUTED-PYRIMIDIN-6-YL (THIONO)-PHOSPHORIC (PHOSPHONIC) ACID ESTERS OR ESTER AMIDES

The present invention relates to and has for its objects the provision of particular new 4-substituted-pyrimidin-6-yl(thiono)-phosphoric (phosphonic) acid esters or ester-amides which possess arthropodicidal and nematicidal properties, active compositions in the form of mixtures of such compounds with solid and liquid dispersible carrier vehicles, and method for producing such compounds and for using such compounds in a new way especially for combating pests, e.g. arthropods and nematodes, with other and further objects becoming apparent from a study of the within specification and accompanying examples.

It is already known that pyrimidinylthionophosphonic acid esters, for example O-(2,4-dimethylpyrimidin-6-yl)-O-methyl- and -O-ethyl-thiono-methane- and -ethane-phosphonic acid ester, possess insecticidal and acaricidal properties (see U.S. Pat. No. 3,216,894).

The present invention provides, as new compounds, the substituted pyrimidinyl(thio)-phosphoric(phosphonic) acid esters and ester-amides of the general formula

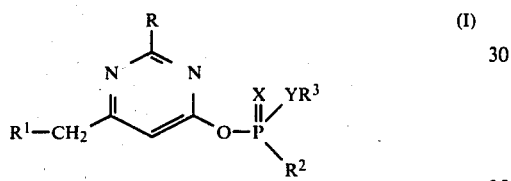

in which
R represents hydrogen, alkyl, alkoxy, alkylthio or alkylamino,
$R^1$ represents halogen, alkoxy, alkylthio or alkylamino,
$R^2$ represents alkyl, alkoxy, alkylamino or phenyl,
$R^3$ represents alkyl and
X and Y, which may be identical or different, represent oxygen or sulphur.

Preferably, R represents hydrogen, straight-chain or branched alkyl with 1 to 6 (especially 1 to 4) carbon atoms or straight-chain or branched alkoxy, alkylthio or dialkylamino with 1 to 4 (especially 1 or 2) carbon atoms in each alkyl radical, $R^1$ represents chlorine, straight-chain or branched alkoxy with 1 to 4 (especially 1 to 3) carbon atoms, straight-chain or branched alkylthio with 1 to 6 (especially 1 to 4) carbon atoms or straight-chain or branched dialkylamino with 1 to 4 (especially 1 or 2) carbon atoms per alkyl radical (especially the alkoxy, alkylthio and dialkylamino radicals mentioned), $R^2$ represents phenyl, straight-chain or branched alkyl with 1 to 6 (especially 1 to 4) carbon atoms, or straight-chain or branched alkoxy or monoalkylamino with 1 to 5 (especially 1 to 4) carbon atoms in the alkyl radical, $R^3$ represents straight-chain or branched alkyl with 1 to 6 (especially 1 to 4) carbon atoms, X represents sulphur and Y represents oxygen or sulphur.

Surprisingly, the substituted pyrimidinyl(thio)-phosphoric (phosphonic) acid esters and ester-amides according to the invention exhibit a better insecticidal, acaricidal and nematicidal action than the previously known pyrimidinylthionophosphoric acid esters of analogous structure and of the same type of action. The compounds according to the invention thus represent a genuine enrichment of the art.

The invention also provides a process for the preparation of a substituted pyrimidinyl(thio)-phosphoric (phosphonic) acid ester or ester-amide of the formula (I) in which a 6-hydroxy-pyrimidine of the general formula

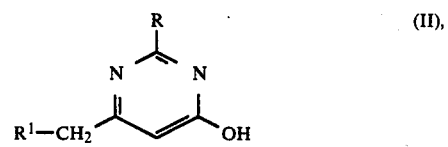

in which
R and $R^1$ have the above-mentioned meanings, is reacted either as such, in the presence of an acid acceptor, or in the form of an alkali metal salt, alkaline earth metal salt or ammonium salt, with a (thio)phosphoric (phosphonic) acid ester halide or ester-amide halide of the general formula

in which
$R^2$, $R^3$, X and Y have the above-mentioned meanings and
Hal represents halogen, especially chlorine, if appropriate in the presence of a solvent or diluent.

If, for example, 6-hydroxy-4-n-propoxymethylpyrimidine and S-ethyl-thiolothionoethanephosphonic acid ester chloride are used as starting materials, the course of the reaction can be represented by the following equation:

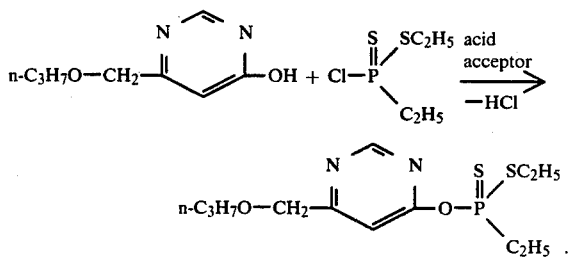

The substituted 6-hydroxy-pyrimidines (II) to be used as starting materials can easily be prepared in accordance with processes known from the literature, for example by halogenating acetoacetic acid alkyl esters, then reacting the product with alkylmercaptides, and closing the ring with amidines.

The following may be mentioned as individual examples of the compounds (II): 4-chloromethyl-, 4-methoxymethyl-, 4-ethoxymethyl-, 4-n-propoxymethyl-, 4-isopropoxymethyl-, 4-methylthiomethyl-, 4-ethylthiomethyl-, 4-n-propylthiomethyl-, 4-iso-propylthiomethyl-, 4-n-butylthiomethyl-, 4-iso-butylthiomethyl-, 4-sec.-butylthiomethyl-, 4-tert.-butylthiomethyl-, 4-dimethylaminomethyl-, 4-diethylaminomethyl-, 2-methyl-4-chloromethyl-, 2-methyl-4-methoxymethyl-, 2-methyl-4-ethoxymethyl-, 2-methyl-4-n-propoxymethyl-, 2- methyl-4-iso-propoxymethyl-, 2-methyl-4-methylthiomethyl-, 2-methyl-4-ethylthiomethyl-, 2-methyl-4-n-propylthiomethyl-, 2-methyl-4-iso-propylthiomethyl-, 2-methyl-4-n-butylthiomethyl-, 2-methyl-4-iso-butylthiomethyl-, 2-methyl-4-sec.-butylthiomethyl-, 2-methyl-4-tert.-butylthiomethyl-, 2-methyl-4-dimethylaminomethyl-, 2-methyl-4-diethylaminomethyl-, 2-ethyl-4-chloromethyl-, 2-ethyl-4-methoxymethyl-, 2-ethyl-4-ethoxymethyl-, 2-ethyl-4-n-propoxymethyl-, 2-ethyl-4-iso-propoxymethyl-, 2-ethyl-4-methylthiomethyl-, 2-ethyl-4-ethylthiomethyl-, 2-ethyl-4-n-propylthiomethyl-, 2-ethyl-4-iso-propylthiomethyl-, 2-ethyl-4-n-butylthiomethyl-, 2-ethyl-4-iso-butylthiomethyl-, 2-ethyl-4-sec.-butylthiomethyl-, 2-ethyl-4-tert.-butylthiomethyl-, 2-ethyl-4-dimethylaminomethyl-, 2-ethyl-4-diethylaminomethyl-, 2-n-propyl-4-chloromethyl-, 2-n-propyl-4-methoxymethyl-, 2-n-propyl-4-ethoxymethyl-, 2-n-propyl-4-n-propoxymethyl-, 2-n-propyl-4-iso-propoxymethyl-, 2-n-propyl-4-methylthiomethyl-, 2-n-propyl-4-ethylthiomethyl-, 2-n-propyl-4-n-propylthiomethyl-, 2-n-propyl-4-iso-propylthiomethyl-, 2-n-propyl-4-n-butylthiomethyl-, 2-n-propyl-4-iso-butylthiomethyl-, 2-n-propyl-4-sec.-butylthiomethyl-, 2-n-propyl-4-tert.-butylthiomethyl-, 2-n-propyl-4-dimethylaminomethyl-, 2-n-propyl-4-diethylaminomethyl-, 2-iso-propyl-4-chloromethyl-, 2-iso-propyl-4-methoxymethyl-, 2-iso-propyl-4-ethoxymethyl-, 2-iso-propyl-4-n-propoxymethyl-, 2-iso-propyl-4-iso-propoxymethyl-, 2-iso-propyl-4-methylthiomethyl-, 2-iso-propyl-4-ethylthiomethyl-, 2-iso-propyl-4-n-propylthiomethyl-, 2-iso-propyl-4-iso-propylthiomethyl-, 2-iso-propyl-4-n-butylthiomethyl-, 2-iso-propyl-4-iso-butylthiomethyl-, 2-iso-propyl-4-sec.-butylthiomethyl-, 2-iso-propyl-4-tert.-butylthiomethyl-, 2-iso-propyl-4-dimethylaminomethyl-, 2-iso-propyl-4-diethylaminomethyl-, 2-n-butyl-4-chloromethyl-, 2-n-butyl-4-methoxymethyl-, 2-n-butyl-4-ethoxymethyl-, 2-n-butyl-4-n-propoxymethyl-, 2-n-butyl-4-iso-propoxymethyl-, 2-n-butyl-4-methylthiomethyl-, 2-n-butyl-4-ethylthiomethyl, 2-n-butyl-4-n-propylthiomethyl-, 2-n-butyl-4-iso-propylthiomethyl-, 2-n-butyl-4-n-butylthiomethyl-, 2-n-butyl-4-iso-butylthiomethyl-, 2-n-butyl-4-sec.-butylthiomethyl-, 2-n-butyl-4-tert.-butylthiomethyl-, 2-n-butyl-4-dimethylaminomethyl-, 2-n-butyl-4-diethylaminomethyl-, 2-iso-butyl-4-chloromethyl-, 2-iso-butyl-4-methoxymethyl-, 2-iso-butyl-4-ethoxymethyl-, 2-iso-butyl-4-n-propoxymethyl-, 2-iso-butyl-4-iso-propoxymethyl-, 2-iso-butyl-4-methylthiomethyl-, 2-iso-butyl-4-ethylthiomethyl-, 2-iso-butyl-4-n-propylthiomethyl-, 2-iso-butyl-4-iso-propylthiomethyl-, 2-iso-butyl-4-n-butylthiomethyl-, 2-iso-butyl-4-iso-butylthiomethyl-, 2-iso-butyl-4-sec.-butylthiomethyl-, 2-iso-butyl-4-tert.-butylthiomethyl-, 2-iso-butyl-4-dimethylaminomethyl-, 2-iso-butyl-4-diethylaminomethyl-, 2-sec.-butyl-4-chloromethyl-, 2-sec.-butyl-4-methoxymethyl-, 2-sec.-butyl-4-ethoxymethyl-, 2-sec.-butyl-4-n-propoxymethyl-, 2-sec.-butyl-4-iso-propoxymethyl-, 2-sec.-butyl-4-methylthiomethyl-, 2-sec.-butyl-4-ethylthiomethyl-, 2-sec.-butyl-4-n-propylthiomethyl-, 2-sec.-butyl-4-iso-propylthiomethyl-, 2-sec.-butyl-4-n-butylthiomethyl-, 2-sec.-butyl-4-iso-butylthiomethyl-, 2-sec.-butyl-4-sec.-butylthiomethyl-, 2-sec.-butyl-4-tert.-butylthiomethyl-, 2-sec.-butyl-4-dimethylaminomethyl-, 2-sec.-butyl-4-diethylaminomethyl-, 2-tert.-butyl-4-chloromethyl-, 2-tert.-butyl-4-methoxymethyl-, 2-tert.-butyl-4-ethoxymethyl-, 2-tert.-butyl-4-n-propoxymethyl-, 2-tert.-butyl-4-iso-propoxymethyl-, 2-tert.-butyl-4-methylthiomethyl-, 2-tert.-butyl-4-ethylthiomethyl-, 2-tert.-butyl-4-n-propylthiomethyl-, 2-tert.-butyl-4-iso-propylthiomethyl-, 2-tert.-butyl-4-n-butylthiomethyl-, 2-tert.-butyl-4-iso-butylthiomethyl-, 2-tert.-butyl-4-sec.-butylthiomethyl-, 2-tert.-butyl-4-tert.-butylthiomethyl-, 2-tert.-butyl-4-dimethylaminomethyl-, 2-tert.-butyl-4-diethylaminomethyl-, 2-methoxy-4-chloromethyl-, 2-methoxy-4-methoxymethyl-, 2-methoxy-4-ethoxymethyl-, 2-methoxy-4-n-propoxymethyl-, 2-methoxy-4-iso-propoxymethyl-, 2-methoxy-4-methylthiomethyl-, 2-methoxy-4-ethylthiomethyl-, 2-methoxy-4-n-propylthiomethyl-, 2-methoxy-4-iso-propylthiomethyl-, 2-methoxy-4-n-butylthiomethyl-, 2-methoxy-4-iso-butylthio-methyl-, 2-methoxy-4-sec.-butylthiomethyl-, 2-methoxy-4-tert.-butylthiomethyl-, 2-methoxy-4-dimethylaminomethyl-, 2-methoxy-4-diethylaminomethyl-, 2-ethoxy-4-chloromethyl-, 2-ethoxy-4-methoxymethyl-, 2-ethoxy-4-ethoxymethyl-, 2-ethoxy-4-n-propoxymethyl-, 2-ethoxy-4-iso-propoxymethyl-, 2-ethoxy-4-methylthiomethyl-, 2-ethoxy-4-ethylthiomethyl-, 2-ethoxy-4-n-propylthiomethyl-, 2-ethoxy-4-iso-propylthiomethyl-, 2-ethoxy-4-n-butylthiomethyl-, 2-ethoxy-4-iso-butylthiomethyl-, 2-ethoxy-4-sec.-butylthiomethyl-, 2-ethoxy-4-tert.-butylthiomethyl-, 2-ethoxy-4-dimethylaminomethyl-, 2-ethoxy-4-diethylaminomethyl-, 2-methylthio-4-chloromethyl-, 2-methylthio-4-methoxymethyl-, 2-methylthio-4-ethoxymethyl-, 2-methylthio-4-n-propoxymethyl-, 2-methylthio-4-iso-propoxymethyl-, 2-methylthio-4-methylthiomethyl-, 2-methylthio-4-ethylthiomethyl-, 2-methylthio-4-n-propylthiomethyl-, 2-methylthio-4-iso-propylthiomethyl-, 2-methylthio-4-n-butylthiomethyl-, 2-methylthio-4-iso-butylthiomethyl-, 2-methylthio-4-sec.-butylthiomethyl-, 2-methylthio-4-tert.-butylthiomethyl-, 2-methylthio-4-dimethylaminomethyl-, 2-methylthio-4-diethylaminomethyl-, 2-ethylthio-4-chloromethyl-, 2-ethylthio-4-methoxymethyl-, 2-ethylthio-4-ethoxymethyl-, 2-ethylthio-4-n-propoxymethyl-, 2-ethylthio-4-iso-propoxymethyl-, 2-ethylthio-4-methylthiomethyl-, 2-ethylthio-4-ethylthiomethyl-, 2-ethylthio-4-n-propylthiomethyl-, 2-ethylthio-4-iso-propylthiomethyl-, 2-ethylthio-4-n-butylthiomethyl-, 2-ethylthio-4-iso-butylthiomethyl-, 2-ethylthio-4-sec.-butylthiomethyl-, 2-ethylthio-4-tert.-butylthiomethyl-, 2-ethylthio-4-dimethylaminomethyl-, 2-ethylthio-4-diethylaminomethyl-, 2-dimethylamino-4-chloromethyl-, 2-dimethylamino-4-methoxymethyl-, 2-dimethylamino-4-ethoxymethyl-, 2-dimethylamino-4-n-propoxymethyl-, 2-dimethylamino-4-iso-propoxymethyl-, 2-dimethylamino-4-methylthiomethyl-, 2-dimethylamino-4-ethylthiomethyl-, 2-dimethylamino-4-n-propylthiomethyl-, 2-dimethylamino-4-isopropylthiomethyl-, 2-dimethylamino-4-n-butylthiomethyl-, 2-dimethylamino-4-iso-butylthiomethyl-, 2-dimethylamino-4-sec.-butylthiomethyl-, 2-dimethylamino-4-diethylaminomethyl-, 2-dimethylamino-4-tert.-butylthiomethyl-, 2-dimethylamino-4-dimethylaminomethyl-, 2-diethylamino-4-chloromethyl-, 2-diethylamino-4-methoxymethyl-, 2-diethylamino-4-ethoxymethyl-, 2-diethylamino-4-n-propoxymethyl-, 2-diethylamino-4-iso-propoxymethyl-, 2-diethylamino-4-methylthiomethyl-, 2-diethylamino-4-ethylthiomethyl-, 2-diethylamino-4-n-propylthiomethyl-, 2-diethylamino-iso-propylthiomethyl-, 2-diethylamino-4-n-butylthiomethyl-, 2-diethylamino-4-iso-butylthiomethyl-, 2-diethylamino-4-sec.-butylthiomethyl-, 2-diethylamino-4-tert.-butylthiomethyl-, 2-diethylamino-4-dimethylaminomethyl- and 2-diethylamino-4-diethylaminomethyl-6-hydroxypyrimidine.

The (thio)phosphoric (phosphonic) acid ester halides and ester-amide halides (III) also to be used as starting materials are known from the literature and can be prepared in accordance with customary processes.

The following may be mentioned as individual examples of the compounds (III): O,O-dimethyl-, O,O-diethyl-, O,O-di-n-propyl, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-ethyl-O-n-propyl-, O-ethyl-O-iso-propyl-, O-ethyl-O-n-butyl-, O-ethyl-O-iso-butyl-, O-ethyl-O-sec.-butyl-, O-n-propyl-O-n-butyl-, O-n-propyl-O-iso-butyl-, O-n-propyl-O-sec.-butyl-, O-iso-propyl-O-n-butyl-, O-iso-propyl-O-iso-butyl- and O-iso-propyl-O-sec.-butyl-phosphoric acid diester chloride and the corresponding thiono analogues; O,S-dimethyl-, O,S-diethyl-, O,S-di-n-propyl-, O,S-di-iso-propyl-, O,S-di-n-butyl-, O,S-di-iso-butyl-, O,S-di-sec.-butyl-, O-methyl-S-n-propyl-, O-ethyl-S-n-propyl-, O-ethyl-S-iso-propyl-, O-ethyl-S-n-butyl-, O-ethyl-S-sec.-butyl-, O-ethyl-S-iso-butyl-, O-n-propyl-S-ethyl-, O-n-propyl-S-iso-propyl-, O-n-butyl-S-n-propyl- and O-sec.-butyl-S-ethyl-thiophosphoric acid diester chloride and the corresponding thiono analogues; O-methyl-, O-ethyl-, O-n-propyl-, O-iso-propyl-, O-n-butyl-, O-iso-butyl-, O-sec.-butyl- and O-tert.-butylmethane-, -ethane,-n-propane-, -iso-propane-, -n-butane-, -iso-butane-, -sec.-butane- and phenyl-phosphonic acid ester chloride and the corresponding thiono analogues; S-methyl-, S-ethyl-, S-n-propyl-, S-iso-propyl-, S-n-butyl-, S-iso-butyl-, S-sec.-butyl- and S-tert.-butyl-methane-, -ethane-, -n-propane-, -iso-propane-, -n-butane-, -iso-butane-, -sec.-butane- and -phenyl-thiophosphonic acid ester chloride and the corresponding thiono analogues; O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-isopropyl-, O-iso-propyl-N-methyl-, O-iso-propyl-N-ethyl-, O-iso-propyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl- and O-sec.-butyl-N-iso-propyl-phosphoric acid ester-amide chloride and the corresponding thiono analogues; and S-methyl-N-methyl-, S-methyl-N-ethyl-, S-methyl-N-n-propyl-, S-methyl-N-iso-propyl-, S-ethyl-N-methyl-, S-ethyl-N-ethyl-, S-ethyl-N-n-propyl-, S-ethyl-N-iso-propyl-, S-n-propyl-N-methyl-, S-n-propyl-N-ethyl-, S-n-propyl-N-n-propyl-, S-n-propyl-N-iso-propyl-, S-iso-propyl-N-methyl-, S-iso-propyl-N-ethyl-, S-iso-propyl-N-n-propyl-, S-iso-propyl-N-iso-propyl-, S-n-butyl-N-methyl-, S-n-butyl-N-ethyl-, S-n-butyl-N-n-propyl-, S-n-butyl-N-iso-propyl-, S-iso-butyl-N-methyl-, S-iso-butyl-N-ethyl-, S-iso-butyl-N-n-propyl-, S-iso-butyl-N-iso-propyl-, S-ec.-butyl-N-methyl-, S-sec.-butyl-N-ethyl-, S-sec.-butyl-N-n-propyl- and S-sec.-butyl-N-iso-propyl-thiolphosphoric acid ester-amide chloride and the corresponding thiono analogues.

The process for the preparation of the compounds according to the invention is preferably carried out in the presence of a suitable solvent or diluent. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, such as diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate or tert.-butylate, have proved particularly suitable, as have aliphatic, aromatic or heterocyclic amines, for example trimethylamine, triethylamine, dimethylaniline, dimethylbenzylamine and pyridine.

The reaction temperature can be varied within a substantial range. In general, the reaction is carried out at from 0° to 120° C., preferably at from 20° to 80° C.

In general, the reaction is allowed to take place under normal pressure.

In general, to carry out the process, the 6-hydroxypyrimidine (II), preferably in 10% molar excess, is stirred in a solvent, in the presence of an acid acceptor, at an elevated temperature for some time, and the phosphoric acid derivative (III) is added to the cooled solution. After completion of the reaction, the mixture is diluted with water and extracted by shaking with an organic solvent, and the organic phase is worked up in the usual manner by drying and distilling off the solvent.

The new compounds are mostly obtained in the form of oils, which in some cases cannot be distilled without decomposition, but can be freed from the last volatile constituents by so-called "slight distillation," that is to say prolonged heating under reduced pressure to moderately elevated temperatures, and can be purified in this way. They are characterised by the refractive index. Some products are obtained in a crystalline form; they are characterised by their melting point.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites such as parasitic fly larvae.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin, hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.000000-100, preferably 0.01-10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

Furthermore, the present invention contemplates methods of selectively killing, combating or controlling pests, e.g. arthropods and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

The starting materials (II) required for the preparation of the compounds according to the invention were prepared, for example, as described below:

(a) Cl—CH$_2$—CO—CH$_2$—CO—OC$_2$H$_5$ 72 g (1 mol) of chlorine were passed into a solution of 84 g (1 mol) of diketene in dry carbon tetrachloride at −20° C. and the reaction solution was then added dropwise, while stirring, to 200 ml of ethanol, during which addition the temperature was not permitted to exceed 0° C.; the solvent was then stripped off on a rotary evaporator and the residue was distilled. 155 g (94% of theory) of γ-chloroacetoacetic acid ethyl ester of boiling point 90° C./7 mm Hg were obtained.

(b) C$_2$H$_5$O—CH$_2$—CO—CH$_2$—CO—OC$_2$H$_5$ 2.2 moles of sodium ethylate in ethanol—prepared from 55.2 g (2.2 moles) of sodium in 500 ml of ethanol—were diluted with 500 ml of tetrahydrofuran. 164.5 g (1 mol) of γ-chloroacetoacetic acid ethyl ester were added to the solution, at room temperature, sufficiently rapidly that the reaction temperature rose to 50° C., the mixture was then cooled to room temperature, 72 g (1.2 mol) of glacial acetic acid were added, the solvent was evaporated off on a rotary evaporator, the residue was shaken with 250 ml of water and extracted twice with 250 ml of methylene chloride at a time, and the combined organic phases were dried over magnesium sulphate. The solvent was stripped off under reduced pressure and the residue was distilled. 123.6 g (71% of theory) of γ-ethoxyacetoacetic acid ethyl ester of boiling point 75° C./3 mm Hg were thus obtained.

γ-Methoxyacetoacetic acid methyl ester, having a boiling point of 76° C./7 mm Hg, was prepared analogously, in a yield of 63% of theory.

(c) n—C$_3$H$_7$S—CH$_2$—CO—CH$_2$—CO—OC$_2$H$_5$ 367 g (2.3 mol) of bromine were added dropwise in the course of 90 minutes at 0° C. to a solution of 300 g (2.3 mol) of acetoacetic acid ethyl ester in 350 ml of ether, the mixture was then stirred further for 1 hour at room temperature, 500 ml of water were added while cooling with ice, the phases were separated and the ether solution was washed once with 100 ml of a 10% strength sodium bicarbonate solution. The organic phase was dried over magnesium sulphate and added dropwise, at room temperature, to an ethanolic solution of 2 moles of sodium propylmercaptide, prepared from 46 g (2 moles) of sodium, 600 g of ethanol and 152 g (2 moles) of n-propylmercaptan. The batch was stirred for a further hour at room temperature and was then extracted by shaking with 2 moles of sodium hydroxide solution (1,334 g of a 6% strength solution), the ether layer was discarded, the aqueous solution was acidified to pH ca.2 with concentrated hydrochloric acid and was extracted by shaking 3 times with 300 ml of methylene chloride, the combined organic phases were dried over magnesium sulphate and the solvent was distilled off. After distilling the residue, 200 g (50% of theory) of γ-n-propylmercaptoacetoacetic acid ethyl ester of boiling point 85° C./0.7 mm Hg were obtained.

The following were prepared analogously:

γ-Methylmercaptoacetoacetic acid ethyl ester in 49% yield, and with a boiling point of 100° C./2 mm Hg.

γ-Ethylmercaptoacetoacetic acid ethyl ester in 56% yield, and with a boiling point of 99° C./1 mm Hg.

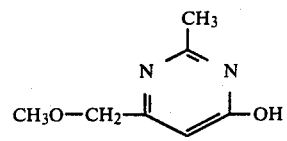

(d)

968 g (4 mol) of sodium methylate in methanol were added to a solution of 187 g (2 mol) of acetamidine hydrochloride and 292 g (2 mol) of γ-methoxyacetoacetic acid methyl ester in 1,000 ml of methanol at 5° C., the mixture was warmed for 3 hours at 50° C. and the solvent was then stripped off under reduced pressure. The residue was dissolved in 500 ml of ice-water and brought to pH ca.6 with concentrated hydrochloric acid, while cooling externally, the precipitate was filtered off, washed with ether and then dried in a desiccator over phosphorus pentoxide. 180 g (58% of theory) of 2-methyl-4-methoxymethyl-6-hydroxy-pyrimidine were obtained in the form of a white powder of melting point 168°–170° C.

The following compounds of the formula

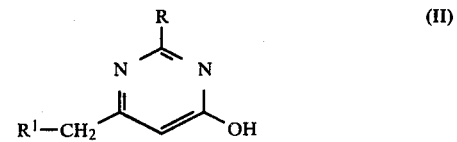

(II)

could be prepared analogously:

Table 1

| R | R$^1$ | Yield (% of theory) | Melting point °C. |
|---|---|---|---|
| [1]CH$_3$S— | n-C$_3$H$_7$S— | 61 | 125 |
| H | n-C$_3$H$_7$S— | 54 | 97 |
| CH$_3$ | n-C$_3$H$_7$S— | 58 | 76 |
| iso-C$_3$H$_7$ | n-C$_3$H$_7$S— | 66 | 112 |
| [2]CH$_3$ | Cl | 57 | 169 |
| H | CH$_3$O— | 50 | 157–160 |
| [1]CH$_3$S— | CH$_3$O— | 82 | 187–190 |
| CH$_3$ | CH$_3$O— | 58 | 168–170 |
| iso-C$_3$H$_7$ | CH$_3$O— | 41 | 148 |
| CH$_3$O— | CH$_3$O— | 62 | 185 |
| (CH$_3$)$_2$N— | C$_2$H$_5$O— | 53 | 129–131 |
| (CH$_3$)$_2$N— | CH$_3$S— | 43 | 163–165 |
| CH$_3$ | C$_3$S— | 56 | 123–125 |
| (C$_2$H$_5$)$_2$N— | CH$_3$S— | 59 | 140–142 |
| CH$_3$O— | CH$_3$S— | 44 | 120–130 |

Notes:
[1]The 2-alkylthio-6-hydroxy-pyrimidines could also be synthesized in two stages, that is to say reacton of the acetoacetic acid ester with thiourea to give 2-mercapto-6-hydroxy-pyrimidine and subsequent alkylation at the sulphur.
[2]Deviating from the above-mentioned instructions, the reaction was, in this case, carried out at −5° to 0° C.; the mixture was subsequently stirred for a further 12 hours at 0° C.

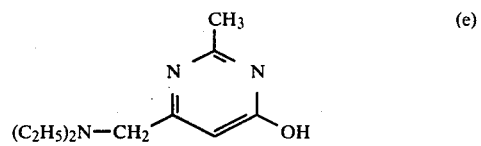

(e)

A mixture of 75 g of 4-chloromethyl-2-methyl-6-hydroxy-pyrimidine prepared as described under (d), 73 g (1 mol) of diethylamine, 300 ml of water and 300 ml of ethanol was heated for two hours under reflux and then evaporated to dryness, 500 ml of acetone were added and the mixture was freed, by filtration, from the hydrochloride which had separated out. The acetone solution was then concentrated, the solid residue was stirred with ether and filtered off and the solid was dried under reduced pressure over phosphorus pentoxide. 60 g (62% of theory) of 4-diethylaminomethyl-2-methyl-6-hydroxy-pyrimidine remained in the form of a white powder of melting point 112° C.

EXAMPLE 2

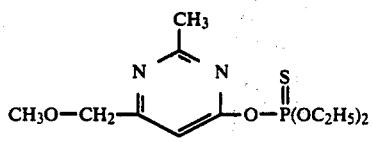

(1)

A mixture of 150 ml of acetonitrile, 8.4 g (55 mmol) of 2-methyl-4-methoxymethyl-6-hydroxy-pyrimidine and 8.4 g (60 mmol) of potassium carbonate was stirred for one hour at 50° C. The mixture was then cooled to room temperature and 9.4 g (50 mmol) of O,O-diethylthiono- phosphoric acid diester chloride were added. After stirring for one hour at 50° C., the reaction solution was extracted by shaking with 200 ml of water and with 300 ml of toluene, the organic phase was dried over magnesium sulphate and after filtration the toluene was stripped off on a rotary evaporator under reduced pressure. 15 g (98% of theory) of O,O-diethyl-O-(2-methyl-4-methoxymethylpyrimidin-6-yl)-thionophosphoric acid ester remained in the form of a yellow oil having a refractive index $n_D^{22}$ of 1.4971.

The following compounds of the formula

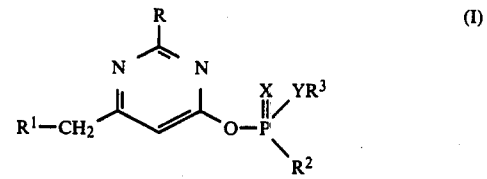

(I)

could be prepared analogously:

Table 2

| Compound No. | R | $R^1$ | $R^2$ | $R^3$ | X | Y | Yield (% of theory) | Refractive index |
|---|---|---|---|---|---|---|---|---|
| 2 | $CH_3S-$ | $n-C_3H_7S-$ | $C_2H_5$ | $C_2H_5$ | S | O | 87 | $n_D^{23}$:1.5585 |
| 3 | $CH_3S-$ | $n-C_3H_7S-$ | $C_2H_5O-$ | $C_2H_5$ | S | O | 94 | $n_D^{23}$:1.5470 |
| 4 | H | $n-C_3H_7S-$ | $C_2H_5$ | $C_2H_5$ | S | O | 81 | $n_D^{23}$:1.5279 |
| 5 | H | $n-C_3H_7S-$ | $C_2H_5O-$ | $C_2H_5$ | S | O | 95 | $n_D^{23}$:1.5211 |
| 6 | $CH_3$ | $n-C_3H_7S-$ | $C_2H_5$ | $C_2H_5$ | S | O | 94 | $n_D^{23}$:1.5237 |
| 7 | $CH_3$ | $n-C_3H_7S-$ | $C_2H_5O-$ | $C_2H_5$ | S | O | 93 | $n_D^{23}$:1.5220 |
| 8 | $CH_3$ | $n-C_3H_7S-$ | $CH_3O-$ | $CH_3$ | S | O | 79 | $n_D^{23}$:1.5265 |
| 9 | $CH_3$ | $n-C_3H_7S-$ | $CH_3$ | $iso-C_3H_7$ | S | O | 90 | $n_D^{23}$:1.5128 |
| 10 | $CH_3$ | $n-C_3H_7S-$ | $C_2H_5O-$ | $C_2H_5$ | O | O | 90 | $n_D^{23}$:1.4928 |
| 11 | $iso-C_3H_7$ | $n-C_3H_7S-$ | $C_2H_5$ | $C_2H_5$ | S | O | 88 | $n_D^{23}$:1.5209 |
| 12 | $iso-C_3H_7$ | $n-C_3H_7S-$ | $C_2H_5O-$ | $C_2H_5$ | S | O | 79 | $n_D^{23}$:1.5105 |
| 13 | $iso-C_3H_7$ | $n-C_3H_7S-$ | $CH_3O-$ | $CH_3$ | S | O | 91 | $n_D^{23}$:1.4991 |
| 14 | $iso-C_3H_7$ | $n-C_3H_7S-$ | $C_2H_5O-$ | $n-C_3H_7$ | S | S | 98 | $n_D^{23}$:1.5270 |
| 15 | $iso-C_3H_7$ | $n-C_3H_7S-$ | $C_2H_5O-$ | $C_2H_5$ | O | O | 90 | $n_D^{23}$:1.4905 |
| 16 | $iso-C_3H_7$ | $n-C_3H_7S-$ | $CH_3$ | $C_2H_5$ | S | O | 86 | $n_D^{23}$:1.5180 |
| 17 | $iso-C_3H_7$ | Cl | $CH_3$ | $iso-C_3H_7$ | S | O | 88 | $n_D^{23}$:1.5179 |
| 18 | $iso-C_3H_7$ | Cl | $C_2H_5$ | $C_2H_5$ | S | O | 87 | $n_D^{23}$:1.5086 |
| 19 | $CH_3$ | Cl | $C_2H_5$ | $C_2H_5$ | S | O | 88 | $n_D^{23}$:1.5246 |
| 20 | $CH_3$ | Cl | $C_2H_5O-$ | $C_2H_5$ | S | O | 78 | $n_D^{23}$:1.5110 |
| 21 | $CH_3$ | Cl | ⏣ | $C_2H_5$ | S | O | 76 | $n_D^{23}$:1.5750 |
| 22 | $CH_3$ | Cl | $CH_3$ | $iso-C_3H_7$ | S | O | 75 | $n_D^{23}$:1.5162 |
| 23 | $CH_3$ | Cl | $CH_3O-$ | $CH_3$ | S | O | 90 | $n_D^{23}$:1.5110 |
| 24 | H | $CH_3O-$ | $C_2H_5$ | $C_2H_5$ | S | O | 94 | $n_D^{23}$:1.5185 |
| 25 | H | $CH_3O-$ | $CH_3$ | $sec.-C_4H_9$ | S | S | 65 | $n_D^{23}$:1.5529 |
| 26 | H | $CH_3O-$ | $C_2H_5O-$ | $C_2H_5$ | S | O | 86 | $n_D^{23}$:1.5089 |
| 27 | H | $CH_3O-$ | $C_2H_5O-$ | $n-C_3H_7$ | S | S | 72 | $n_D^{23}$:1.5332 |
| 28 | H | $CH_3O-$ | $CH_3$ | $iso-C_3H_7$ | S | O | 83 | $n_D^{23}$:1.5135 |
| 29 | H | $CH_3O-$ | ⏣ | $C_2H_5$ | S | O | 72 | $n_D^{23}$:1.5632 |
| 30 | H | $CH_3O-$ | $C_2H_5O-$ | $C_2H_5$ | O | O | 91 | $n_D^{23}$:1.4731 |
| 31 | H | $CH_3O-$ | $CH_3O-$ | $CH_3$ | S | O | 60 | $n_D^{23}$:1.5319 |
| 32 | H | $CH_3O-$ | $CH_3$ | $C_2H_5$ | S | O | 86 | $n_D^{23}$:1.5180 |
| 33 | H | $CH_3O-$ | $C_2H_5$ | $CH_3$ | S | O | 89 | $n_D^{23}$:1.5252 |
| 34 | H | $CH_3O-$ | $sec.-C_4H_9$ | $C_2H_5$ | S | O | 59 | $n_D^{23}$:1.5141 |
| 35 | $CH_3S-$ | $CH_3O-$ | $C_2H_5$ | $C_2H_5$ | S | O | 89 | $n_D^{23}$:1.5479 |
| 36 | $CH_3S-$ | $CH_3O-$ | $CH_3$ | $sec.-C_4H_9$ | S | S | 68 | $n_D^{23}$:1.5780 |
| 37 | $CH_3S-$ | $CH_3O-$ | $C_2H_5O-$ | $C_2H_5$ | S | O | 85 | $n_D^{23}$:1.5329 |
| 38 | $CH_3S-$ | $CH_3O-$ | $C_2H_5O-$ | $n-C_3H_7$ | S | S | 75 | $n_D^{23}$:1.5552 |
| 39 | $CH_3S-$ | $CH_3O-$ | ⏣ | $C_2H_5$ | S | O | 74 | $n_D^{23}$:1.5850 |
| 40 | $CH_3S-$ | $CH_3O-$ | $CH_3$ | $iso-C_3H_7$ | S | O | 94 | $n_D^{23}$:1.5060 |
| 41 | $CH_3S-$ | $CH_3O-$ | $C_2H_5O-$ | $C_2H_5$ | O | O | 89 | $n_D^{23}$:1.5422 |
| 42 | $CH_3S-$ | $CH_3O-$ | $CH_3O-$ | $CH_3$ | S | O | 64 | $n_D^{23}$:1.5392 |

Table 2-continued

| Compound No. | R | R¹ | R² | R³ | X | Y | Yield (% of theory) | Refractive index |
|---|---|---|---|---|---|---|---|---|
| 43 | $CH_3S-$ | $CH_3O-$ | $CH_3$ | $C_2H_5$ | S | O | 88 | $n_D^{23}$:1.5525 |
| 44 | $CH_3S-$ | $CH_3O-$ | $C_2H_5$ | $CH_3$ | S | O | 97 | $n_D^{23}$:1.5412 |
| 45 | $CH_3S-$ | $CH_3O-$ | sec.-$C_4H_9$ | $C_2H_5$ | S | O | 99 | $n_D^{23}$:1.5408 |
| 46 | $CH_3S-$ | $CH_3O-$ | iso-$C_3H_7NH-$ | $C_2H_5$ | S | O | 78 | $n_D^{23}$:1.5402 |
| 47 | $CH_3S-$ | $CH_3O-$ | $C_2H_5O-$ | n-$C_3H_7$ | S | O | 86 | $n_D^{23}$:1.5290 |
| 48 | $CH_3S-$ | $CH_3O-$ | $CH_3O-$ | n-$C_3H_7$ | S | O | 85 | $n_D^{23}$:1.5312 |
| 49 | $CH_3S-$ | $CH_3O-$ | $CH_3$ | n-$C_3H_7$ | S | S | 98 | $n_D^{23}$:1.5815 |
| 50 | $CH_3S-$ | $CH_3O-$ | n-$C_3H_7O-$ | iso-$C_3H_7$ | S | O | 94 | $n_D^{23}$:1.5200 |
| 51 | $CH_3S-$ | $CH_3O-$ | $CH_3$ | $CH_3$ | S | S | 87 | $n_D^{23}$:1.5972 |
| 52 | $CH_3$ | $CH_3O-$ | $CH_3O-$ | $CH_3$ | S | O | 75 | $n_D^{22}$:1.5129 |
| 53 | $CH_3$ | $CH_3O-$ | $CH_3$ | iso-$C_3H_7$ | S | O | 96 | $n_D^{22}$:1.5084 |
| 54 | $CH_3$ | $CH_3O-$ | $CH_3$ | $C_2H_5$ | S | O | 80 | $n_D^{22}$:1.5149 |
| 55 | $CH_3$ | $CH_3O-$ | $C_2H_5$ | $CH_3$ | S | O | 79 | $n_D^{22}$:1.5174 |
| 56 | $CH_3$ | $CH_3O-$ |  | $C_2H_5$ | S | O | 76 | $n_D^{22}$:1.5611 |
| 57 | $CH_3$ | $CH_3O-$ | $C_2H_5$ | $C_2H_5$ | S | O | 89 | $n_D^{22}$:1.5082 |
| 58 | $CH_3$ | $CH_3O-$ | $C_2H_5O-$ | n-$C_3H_7$ | S | S | 89 | $n_D^{22}$:1.5302 |
| 59 | $CH_3$ | $CH_3O-$ | $C_2H_5O-$ | $C_2H_5$ | O | O | 72 | $n_D^{22}$:1.4724 |
| 60 | $CH_3$ | $CH_3O-$ | $C_2H_5O-$ | n-$C_3H_7$ | S | O | 94 | $n_D^{22}$:1.4958 |
| 61 | $CH_3$ | $CH_3O-$ | $CH_3O-$ | n-$C_3H_7$ | S | O | 65 | $n_D^{22}$:1.5004 |
| 62 | $CH_3$ | $CH_3O-$ | n-$C_3H_7O-$ | iso-$C_3H_7$ | S | O | 74 | $n_D^{22}$:1.4890 |
| 63 | $CH_3$ | $CH_3O-$ | $C_2H_5$ | sec.-$C_4H_9$ | S | S | 94 | $n_D^{22}$:1.5448 |
| 64 | iso-$C_3H_7$ | $CH_3O-$ | $C_2H_5$ | $C_2H_5$ | S | O | 92 | $n_D^{22}$:1.5040 |
| 65 | iso-$C_3H_7$ | $CH_3O-$ | $CH_3$ | sec.-$C_4H_9$ | S | S | 73 | $n_D^{22}$:1.5406 |
| 66 | iso-$C_3H_7$ | $CH_3O-$ | $C_2H_5O-$ | $C_2H_5$ | S | O | 72 | $n_D^{22}$:1.4931 |
| 67 | iso-$C_3H_7$ | $CH_3O-$ | $C_2H_5O-$ | n-$C_3H_7$ | S | S | 70 | $n_D^{22}$:1.5209 |
| 68 | iso-$C_3H_7$ | $CH_3O-$ |  | $C_2H_5$ | S | O | 76 | $n_D^{22}$:1.5501 |
| 69 | iso-$C_3H_7$ | $CH_3O-$ | $CH_3$ | iso-$C_3H_7$ | S | O | 82 | $n_D^{22}$:1.5014 |
| 70 | iso-$C_3H_7$ | $CH_3O-$ | $C_2H_5O-$ | $C_2H_5$ | O | O | 79 | $n_D^{22}$:1.5103 |
| 71 | iso-$C_3H_7$ | $CH_3O-$ | $CH_3O-$ | $CH_3$ | S | O | 82 | $n_D^{22}$:1.5240 |
| 72 | iso-$C_3H_7$ | $CH_3O-$ | $CH_3$ | $C_2H_5$ | S | O | 92 | $n_D^{22}$:1.5044 |
| 73 | iso-$C_3H_7$ | $CH_3O-$ | $C_2H_5$ | $CH_3$ | S | O | 83 | $n_D^{22}$:1.5049 |
| 74 | iso-$C_3H_7$ | $CH_3O-$ | sec.-$C_4H_9$ | $C_2H_5$ | S | O | 88 | $n_D^{22}$:1.5032 |
| 75 | iso-$C_3H_7$ | $CH_3O-$ | iso-$C_3H_7NH-$ | $C_2H_5$ | S | O | 58 | $n_D^{22}$:1.5039 |
| 76 | iso-$C_3H_7$ | $CH_3O-$ | $C_2H_5O-$ | n-$C_3H_7$ | S | O | 93 | $n_D^{20}$:1.4939 |
| 77 | iso-$C_3H_7$ | $CH_3O-$ | $CH_3O-$ | n-$C_3H_7$ | S | O | 75 | $n_D^{20}$:1.4940 |
| 78 | iso-$C_3H_7$ | $CH_3O-$ | $CH_3$ | n-$C_3H_7$ | S | S | 61 | $n_D^{20}$:1.5012 |
| 79 | iso-$C_3H_7$ | $CH_3O-$ | iso-$C_3H_7O-$ | n-$C_3H_7$ | S | O | 56 | $n_D^{20}$:1.4861 |
| 80 | $(C_2H_5)_2N-$ | n-$C_3H_7S-$ | $C_2H_5$ | $C_2H_5$ | S | O | 79 | $n_D^{23}$:1.5043 |
| 81 | $(C_2H_5)_2N-$ | n-$C_3H_7S-$ | $C_2H_5O-$ | $C_2H_5$ | S | O | 70 | $n_D^{23}$:1.4830 |
| 82 | $CH_3O-$ | $CH_3O-$ | $C_2H_5O-$ | $C_2H_5$ | S | O | 78 | $n_D^{23}$:1.5044 |
| 83 | $CH_3O-$ | $CH_3O-$ | $C_2H_5$ | $CH_3$ | S | O | 69 | $n_D^{23}$:1.5245 |
| 84 | $CH_3O-$ | $CH_3O-$ | $C_2H_5O-$ | n-$C_3H_7$ | S | S | 68 | $n_D^{23}$:1.5353 |
| 85 | $CH_3O-$ | $CH_3O-$ | $CH_3$ | $C_2H_5$ | S | O | 75 | 64 (m.pt.) |
| 86 | $CH_3O-$ | $CH_3O-$ |  | $C_2H_5$ | S | O | 68 | $n_D^{23}$:1.5631 |
| 87 | $(CH_3)_2N-$ | $C_2H_5O-$ | $C_2H_5O-$ | $C_2H_5$ | S | O | 60 | $n_D^{20}$:1.5153 |
| 88 | $(CH_3)_2N-$ | $C_2H_5O-$ | $C_2H_5$ | $C_2H_5$ | S | O | 68 | $n_D^{20}$:1.5280 |
| 89 | $(CH_3)_2N-$ | $C_2H_5O-$ | $CH_3O-$ | $CH_3$ | S | O | 78 | $n_D^{20}$:1.5280 |
| 90 | $CH_3$ | $C_2H_5O-$ | $C_2H_5O-$ | $C_2H_5$ | S | O | 73 | $n_D^{20}$:1.4931 |
| 91 | $CH_3$ | $C_2H_5O-$ | $CH_3O-$ | $CH_3$ | S | O | 41 | $n_D^{20}$:1.5030 |
| 92 | $CH_3$ | $C_2H_5O-$ | $C_2H_5$ | $C_2H_5$ | S | O | 78 | $n_D^{20}$:1.5060 |
| 93 | $(CH_3)_2N-$ | $CH_3S-$ | $C_2H_5O-$ | $C_2H_5$ | S | O | 54 | $n_D^{22}$:1.5453 |
| 94 | $(CH_3)_2N-$ | $CH_3S-$ | $C_2H_5$ | $C_2H_5$ | S | O | 62 | $n_D^{22}$:1.5568 |
| 95 | $(CH_3)_2N-$ | $CH_3S-$ | $CH_3O-$ | $CH_3$ | S | O | 56 | $n_D^{22}$:1.5560 |
| 96 | $(CH_3)_2N-$ | $CH_3S-$ | $C_2H_5O-$ | n-$C_3H_7$ | S | S | 53 | $n_D^{22}$:1.5681 |
| 97 | $CH_3$ | $CH_3S-$ | $C_2H_5$ | $C_2H_5$ | S | O | 42 | $n_D^{22}$:1.5431 |
| 98 | $CH_3$ | $CH_3S-$ | $C_2H_5O-$ | $C_2H_5$ | S | O | 66 | $n_D^{22}$:1.5390 |
| 99 | $(CH_3)_2N-$ | $CH_3S-$ | | $C_2H_5$ | S | O | 63 | |
| 100 | $CH_3$ | $CH_3S-$ | $CH_3O-$ | $CH_3$ | S | O | 52 | $n_D^{25}$:1.5630 |
| 101 | $CH_3$ | $CH_3S-$ |  | $C_2H_5$ | S | O | 63 | $n_D^{25}$:1.5855 |
| 102 | $CH_3$ | $CH_3S-$ | iso-$C_3H_7NH-$ | $C_2H_5$ | S | O | 46 | $n_D^{23}$:1.5313 |
| 103 | $CH_3$ | $CH_3S-$ | $C_2H_5O-$ | $C_2H_5$ | O | O | 38 | $n_D^{23}$:1.5114 |
| 104 | $(C_2H_5)_2N-$ | $CH_3S-$ | $C_2H_5O-$ | $C_2H_5$ | S | O | 64 | $n_D^{23}$:1.5340 |
| 105 | $(C_2H_5)_2N-$ | $CH_3S-$ | $C_2H_5O-$ | n-$C_3H_7$ | S | O | 49 | $n_D^{23}$:1.5249 |

Table 2-continued

| Compound No. | R | R¹ | R² | R³ | X | Y | Yield (% of theory) | Refractive index |
|---|---|---|---|---|---|---|---|---|
| 106 | $(C_2H_5)_2N-$ | $CH_3S-$ | $n-C_3H_7O-$ | $CH_3$ | S | O | 22 | $n_D^{23}:1.5268$ |
| 107 | $(C_2H_5)_2N-$ | $CH_3S-$ | $C_2H_5O-$ | $n-C_3H_7$ | S | S | 12 | $n_D^{23}:1.5709$ |
| 108 | $(C_2H_5)_2N-$ | $CH_3S-$ | $CH_3O-$ | $CH_3$ | S | O | 32 | $n_D^{23}:1.5260$ |
| 109 | $CH_3O-$ | $CH_3S-$ | $C_2H_5$ | $C_2H_5$ | S | O | 68 | $n_D^{26}:1.5420$ |
| 110 | $CH_3O-$ | $CH_3S-$ | $CH_3$ | $iso-C_3H_7$ | S | O | 59 | $n_D^{26}:1.5372$ |
| 111 | $iso-C_3H_7$ | $(C_2H_5)_2N-$ | $C_2H_5O-$ | $C_2H_5$ | S | O | 75 | $n_D^{23}:1.5010$ |
| 112 | $iso-C_3H_7$ | $(C_2H_5)_2N-$ | $C_2H_5$ | $C_2H_5$ | S | O | 88 | $n_D^{23}:1.5043$ |
| 113 | $CH_3$ | $(C_2H_5)_2N-$ | $C_2H_5$ | $C_2H_5$ | S | O | | |

The insecticidal, acaricidal or nematicidal activity of the compounds of this invention is illustrated by the following biotest examples wherein the compounds according to the present invention are each identified by the number (given in brackets) from the preparative example, hereinabove.

The known comparison compounds are identified as follows:

(A) = 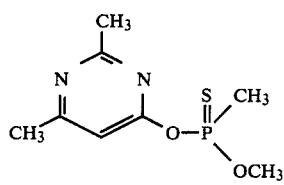

(B) = 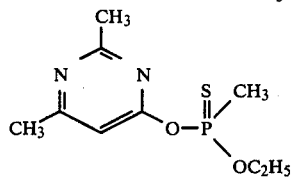

(C) = 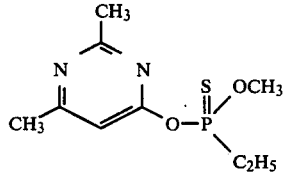

EXAMPLE 3

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamond-back moth (Plutella maculipennis).

After the specified periods of time, the degree of destruction was determined as a percentage: 100% meant that all of the caterpillars were killed whereas 0% meant that none of the caterpillars were killed.

The active compounds, the concentrations of the active compounds, the evaluation times and the results can be seen from the following table:

Table 3

| Active compound | (Plutella test) Active compound concentration in % | Degree of destruction in % after 3 days |
|---|---|---|
| (A) | 0.01 | 100 |
|  | 0.001 | 0 |
| (B) | 0.01 | 100 |
|  | 0.001 | 0 |
| (C) | 0.01 | 100 |
|  | 0.001 | 0 |
| (7) | 0.01 | 100 |
|  | 0.001 | 100 |
| (84) | 0.01 | 100 |
|  | 0.001 | 100 |
| (77) | 0.01 | 100 |
|  | 0.001 | 100 |
| (67) | 0.01 | 100 |
|  | 0.001 | 100 |
| (111) | 0.01 | 100 |
|  | 0.001 | 90 |

EXAMPLE 4

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (Tetranychus urticae) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 4

| Active compound | (Tetranychus test) Active compound concentration in % | Degree of destruction in % after 2 days |
|---|---|---|
| (C) | 0.1 | 20 |
| (30) | 0.1 | 100 |
| (5) | 0.1 | 100 |
| (4) | 0.1 | 100 |
| (28) | 0.1 | 100 |
| (8) | 0.1 | 100 |
| (54) | 0.1 | 100 |
| (9) | 0.1 | 100 |

Table 4-continued

(Tetranychus test)

| Active compound | Active compound concentration in % | Degree of destruction in % after 2 days |
|---|---|---|
| (98) | 0.1 | 100 |
| (7) | 0.1 | 100 |
| (10) | 0.1 | 100 |
| (97) | 0.1 | 100 |
| (6) | 0.1 | 100 |
| (80) | 0.1 | 100 |
| (85) | 0.1 | 100 |
| (110) | 0.1 | 100 |
| (43) | 0.1 | 100 |
| (66) | 0.1 | 100 |
| (12) | 0.1 | 100 |
| (15) | 0.1 | 100 |
| (72) | 0.1 | 100 |
| (16) | 0.1 | 100 |
| (69) | 0.1 | 100 |
| (73) | 0.1 | 100 |
| (64) | 0.1 | 100 |
| (11) | 0.1 | 100 |
| (111) | 0.1 | 100 |

EXAMPLE 5

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 5

(*Phorbia antiqua* grubs in the soil)

| Active compound | Degree if destruction in % at an active compound concentration of 20 ppm |
|---|---|
| (A) | 0 |
| (B) | 0 |
| (C) | 0 |
| (66) | 100 |
| (68) | 100 |
| (69) | 100 |
| (76) | 100 |
| (37) | 100 |
| (47) | 100 |
| (29) | 100 |
| (27) | 100 |
| (34) | 100 |
| (12) | 100 |

Table 5-continued

(*Phorbia antiqua* grubs in the soil)

| Active compound | Degree if destruction in % at an active compound concentration of 20 ppm |
|---|---|
| (16) | 100 |
| (7) | 100 |
| (87) | 100 |
| (88) | 100 |
| (90) | 100 |
| (93) | 100 |
| (98) | 100 |

EXAMPLE 6

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 6

(*Meloidogyne incognita*)

| Active compound | Degree of destruction in % at an active compound concentration of 20 ppm |
|---|---|
| (A) | 0 |
| (B) | 0 |
| (C) | 0 |
| (66) | 100 |
| (67) | 100 |
| (63) | 100 |
| (16) | 100 |
| (14) | 100 |
| (6) | 100 |
| (7) | 100 |

EXAMPLE 7

Mosquito larvae test
Solvent: 3 parts by weight of acetone
Emulsifier: 1 part by weight of alkylaryl polyglycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% meant that all of the larvae were killed. 0% meant that none of the larvae were killed.

The active compounds, the concentrations of the active compounds and the results can be seen from the followimg table:

Table 7

Mosquito larvae test (*Aedes aegypti* larvae)

| Active compound | Active compound concentration of the solution in % | Degree of destruction in % |
|---|---|---|
| (A) | 1 | 0 |
| (B) | 1 | 0 |
| (C) | 1 | 0 |
| (64) | 1 | 100 |
| (66) | 1 | 100 |
| (67) | 1 | 100 |
| (71) | 1 | 100 |
| (76) | 1 | 100 |
| (77) | 0.1 | 100 |
| (52) | 1 | 100 |
| (53) | 1 | 100 |
| (56) | 1 | 100 |
| (57) | 1 | 100 |
| (1) | 1 | 100 |
| (60) | 1 | 100 |
| (61) | 1 | 100 |
| (35) | 1 | 100 |
| (39) | 1 | 100 |
| (40) | 1 | 100 |
| (47) | 1 | 100 |
| (48) | 1 | 100 |
| (30) | 1 | 100 |
| (11) | 1 | 100 |
| (12) | 1 | 100 |
| (13) | 1 | 100 |
| (16) | 1 | 100 |
| (14) | 1 | 100 |
| (6) | 1 | 100 |
| (7) | 1 | 100 |
| (82) | 1 | 100 |
| (83) | 1 | 100 |
| (87) | 1 | 100 |
| (88) | 1 | 100 |
| (90) | 1 | 100 |
| (93) | 1 | 100 |
| (94) | 1 | 100 |
| (95) | 1 | 100 |
| (96) | 1 | 100 |
| (97) | 1 | 100 |
| (98) | 1 | 100 |
| (103) | 1 | 100 |
| (104) | 1 | 100 |
| (105) | 1 | 100 |
| (106) | 1 | 100 |
| (107) | 1 | 100 |
| (108) | 1 | 100 |
| (109) | 1 | 100 |
| (110) | 1 | 100 |

EXAMPLE 8

Test with parasitic fly larvae
Emulsifier: 80 parts by weight of Cremophor EL

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, resistant) were introduced into a test tube which contained about 3 ml of a 20% strength suspension of egg yolk powder in water, and which was fitted with cottonwool plugs of appropriate size. 0.5 ml of the active-compound preparation was placed on this egg-yolk-powder suspension. After 24 hours, the degree of destruction in % was determined. 100% meant that all of the larvae had been killed and 0% meant that none of the larvae had been killed.

The active compound, amounts used and results can be seen from the table which follows:

Table 8

Test with parasitic fly larvae (*Lucilia cuprina* res.)

| Active compound | Active compound concentration in ppm | Degree of destruction in % |
|---|---|---|
| (64) | 100 | 100 |
| | 10 | 100 |
| | 1 | 100 |
| (66) | 100 | 100 |
| | 30 | 100 |
| | 10 | 100 |
| (67) | 100 | 100 |
| | 30 | 100 |
| | 10 | 100 |
| (52) | 100 | 100 |
| | 30 | 100 |
| | 10 | 100 |
| | 3 | 100 |
| | 1 | >50 |
| (53) | 100 | 100 |
| | 10 | 100 |
| | 1 | 100 |
| (56) | 100 | 100 |
| | 10 | 100 |
| | 1 | 100 |
| (57) | 100 | 100 |
| | 10 | 100 |
| | 1 | 100 |
| (54) | 100 | 100 |
| | 30 | 100 |
| | 10 | 100 |
| | 3 | 100 |
| | 1 | 100 |
| (55) | 100 | 100 |
| | 10 | 100 |
| | 1 | 100 |
| (60) | 100 | 100 |
| | 10 | 100 |
| | 1 | 100 |
| (1) | 100 | 100 |
| | 10 | 100 |
| | 1 | 100 |
| (58) | 100 | 100 |
| | 30 | 100 |
| | 10 | >50 |
| | 3 | 0 |
| (63) | 100 | 100 |
| | 10 | 100 |
| | 1 | 100 |
| (62) | 100 | 100 |
| | 30 | 100 |
| | 10 | 100 |
| | 3 | 100 |
| | 1 | 0 |
| (61) | 100 | 100 |
| | 10 | 100 |
| | 1 | 100 |
| (37) | 100 | 100 |
| | 30 | 100 |
| | 10 | >50 |
| | 3 | 0 |
| (42) | 100 | 100 |
| | 30 | 100 |
| | 10 | 100 |
| | 3 | >50 |
| | 1 | 0 |

Table 8-continued

| Active compound | Test with parasitic fly larvae (Lucilia cuprina res.) | |
|---|---|---|
| | Active compound concentration in ppm | Degree of destruction in % |
| (43) | 100 | 100 |
| | 30 | 100 |
| | 10 | 100 |
| | 3 | 0 |

EXAMPLE 9

Test with parasitic scab mites (Psoroptes cuniculi)
Solvent: Cremophor

To produce a suitable preparation of active compound, the active substance in question was mixed with the stated solvent in the ratio of 1:2 and the concentrate thus obtained was diluted with water to the desired concentration.

About 10–25 scab mites (Psoroptes cuniculi) were introduced into 1 ml portions of the active compound preparation to be tested, which had been pipetted into the tablet nests of a blister pack. After 24 hours, the degree of destruction in percent was determined. 100% meant that all of the mites had been killed and 0% meant that none of the mites had been killed.

Active compounds, active compound concentrations and results can be seen from the table which follows:

Table 9

| Active compound | Test with parasitic scab mites (Psoroptes cuniculi) | |
|---|---|---|
| | Active compound concentration in ppm | Degree of destruction in % |
| (58) | 1,000 | 100 |
| | 300 | 100 |
| | 100 | >50 |
| | 30 | >50 |
| (63) | 1,000 | 100 |
| | 100 | 100 |
| (25) | 1,000 | 100 |
| | 300 | 100 |
| | 100 | 100 |
| | 30 | 100 |
| (52) | 1,000 | 100 |
| | 300 | 100 |
| | 100 | 100 |
| (11) | 1,000 | 100 |
| | 300 | 100 |
| | 100 | 100 |
| (16) | 1,000 | 100 |
| | 300 | 100 |
| | 100 | 100 |
| | 30 | 100 |
| | 10 | 100 |
| (6) | 1,000 | 100 |
| | 100 | 100 |
| (7) | 1,000 | 100 |
| | 100 | 100 |

A mixture of 75 g of 4-chloromethyl-2-methyl-6-hydroxy-pyrimidine prepared as described under (d), 73 g (1 mol) of diethylamine, 300 ml of water and 300 ml of ethanol was heated for two hours under reflux and then evaporated to dryness, 500 ml of acetone were added and the mixture was freed, by filtration, from the hydrochloride which had separated out. The acetone solution was then concentrated, the solid residue was stirred with ether and filtered off and the solid was dried under reduced pressure over phosphorus pentoxide. 60 g (62% of theory) of 4-diethylaminomethyl-2-methyl-6-hydroxy-pyrimidine remained in the form of a white powder of melting point 112° C.

It will be appreciated that the instant specification and examples are set forth by way of illustration and not limitation, and that various modifications and changes may be made without departing from the spirit and scope of the present invention.

What is claimed is:

1. A 4-substituted-pyrimidin-6-yl (thiono)-phosphoric (phosphonic) acid ester or ester-amide of the formula

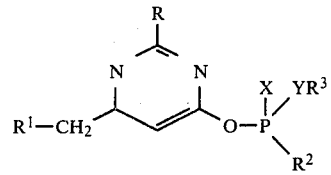

in which
R represents hydrogen, alkyl with 1 to 6 carbon atoms, or alkoxy, alkylthio or alkylamino with 1 to 4 carbon atoms in each alkyl radical,
$R^1$ represents halogen, alkoxy with 1 to 4 carbon atoms, alkylthio with 1 to 6 carbon atoms or alkylamino with 1 to 4 carbon atoms per alkyl radical,
$R^2$ represents alkyl with 1 to 6 carbon atoms, alkoxy with 1 to 5 carbon atoms, alkylamino with 1 to 5 carbon atoms or phenyl,
$R^3$ represents alkyl with 1 to 6 carbon atoms and
X and Y, which may be identical or different, represent oxygen or sulfur.

2. A compound according to claim 1, in which
R represents hydrogen, alkyl with 1 to 6 carbon atoms, or alkoxy, alkylthio or dialkylamino with 1 to 4 carbon atoms in each alkyl radical,
$R^1$ represents chlorine, alkoxy with 1 to 4 carbon atoms, alkylthio with 1 to 6 carbon atoms, or dialkylamino with 1 to 4 carbon atoms per alkyl radical, and
X represents sulphur.

3. A compound according to claim 1, wherein such compound is O,O-diethyl-O-(2-methyl-4-n-propylthiomethylpyrimidin-6-yl)-thionophosphoric acid ester of the formula

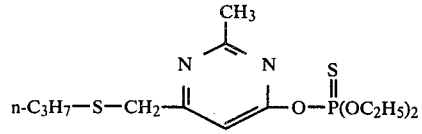

4. A compound according to claim 1, wherein such compound is O,O-diethyl-O-(4-methoxymethylpyrimidin-6-yl)-phosphoric acid ester of the formula

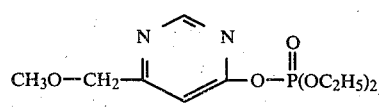

5. A compound according to claim 1, wherein such compound is O-ethyl-O-(2-isopropyl-4-methoxymethylpyrimidin-6-yl)-ethane thiono phosphonic acid ester of the formula

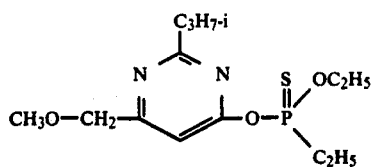

6. A compound according to claim 1, wherein such compound is O,O-diethyl-O-(2-isopropyl-4-methoxymethylpyrimidin-6-yl)-thionophosphoric acid ester of the formula

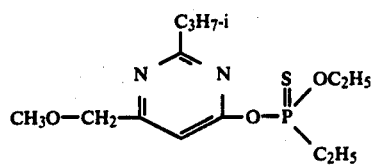

7. A compound according to claim 1, wherein such compound is O,O-diethyl-O-(2-methyl-4-methylthiomethylpyrimidin-6-yl)-thionophosphoric acid ester of the formula

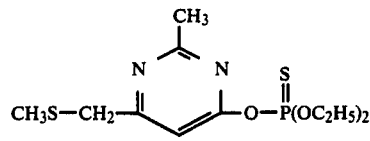

8. An arthropodicidal or nematicidal composition containing as active ingredient on arthropodicidally or nematicidaly effective amount of a compound according to claim 1 in admixture with a diluent.

9. A method of combating arthropods or nematodes, which comprises applying to the arthropods or nematodes, or to a habitat thereof, an arthropodicidally or nematicidally effective amount of a compound according to claim 1.

10. The method according to claim 9, wherein there is applied to a domesticated animal O,O-diethyl-O-(2-methyl-4-n-propylthiomethyl-pyrimidin-6-yl)-thionophosphoric acid ester, O,O-diethyl-O-(4-methoxymethylpyrimidin-6-yl)-phosphoric acid ester, O-ethyl-O-(2-isopropyl-4-methoxymethylpyrimidin-6-yl)-ethane thiono phosphonic acid ester,

* * * * *